United States Patent [19]
Poccia et al.

[11] Patent Number: 5,246,429
[45] Date of Patent: Sep. 21, 1993

[54] ABSORBENT ARTICLE

[75] Inventors: John F. Poccia, Union Beach; Kevin J. Ovans, East Windsor, both of N.J.; Heinz Pieniak, Des Moines, Wash.

[73] Assignee: McNeil-PPC, Inc., New Brunswick, N.J.

[21] Appl. No.: 943,062

[22] Filed: Sep. 10, 1992

Related U.S. Application Data

[62] Division of Ser. No. 772,772, Oct. 7, 1991, Pat. No. 5,171,237, which is a division of Ser. No. 365,967, Jun. 14, 1989, Pat. No. 5,100,397.

[51] Int. Cl.$^5$ .............................................. A61F 13/15
[52] U.S. Cl. ...................................... 604/368; 604/379; 604/365
[58] Field of Search ............. 604/365, 379, 385.1; 428/138

[56] References Cited

U.S. PATENT DOCUMENTS

| | | | |
|---|---|---|---|
| 4,103,062 | 7/1978 | Aberson et al. | 604/368 |
| 4,104,214 | 8/1978 | Meierhoefer | 604/368 |
| 4,105,033 | 8/1978 | Chatterjee et al. | 604/368 |
| 5,021,050 | 6/1991 | Iskra | 604/379 |
| 5,100,397 | 3/1992 | Poccia et al. | 604/365 |
| 5,139,861 | 8/1992 | Williams et al. | 604/379 |
| 5,171,237 | 12/1992 | Poccia et al. | 604/365 |

Primary Examiner—Randall L. Green
Assistant Examiner—Gina M. Gualtieri
Attorney, Agent, or Firm—Dressler, Goldsmith, Shore, Sutker & Milnamow, Ltd.

[57] ABSTRACT

An absorbent mixture, as made from fibers formed into a fibrous web and a polymerizable, cross-linkable material, in a liquid carrier. The material, when polymerized and cross-linked, results in a superabsorbent polymer. The material, in the liquid carrier, is dispersed within the fibrous web, as dispersed inclusions, and is polymerized and cross-linked in situ, within the fibrous web, so as to form a composite web comprising the fibrous web and the superabsorbent polymer, as dispersed particles, at least some of which are bound to fibers from the fibrous web. The composite web is ground, so as to cause some of the superabsorbent polymers to become particulate while fragments of the superabsorbent polymer remain bound to fibers from the fibrous web. Before the composite web is ground, it may be provided with a fibrous layer or fibrous layers in intimate contact therewith, and also compressed.

10 Claims, 2 Drawing Sheets

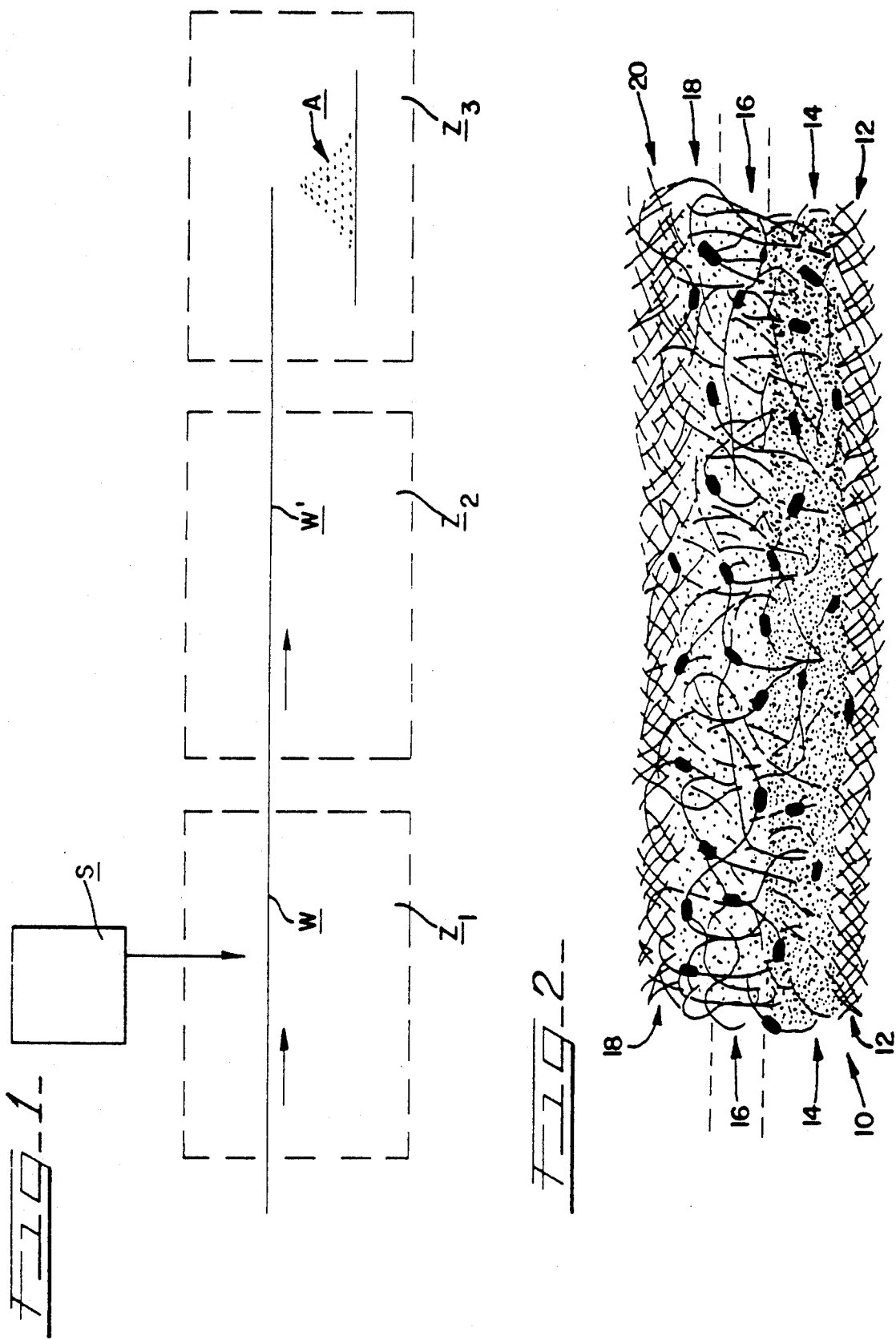

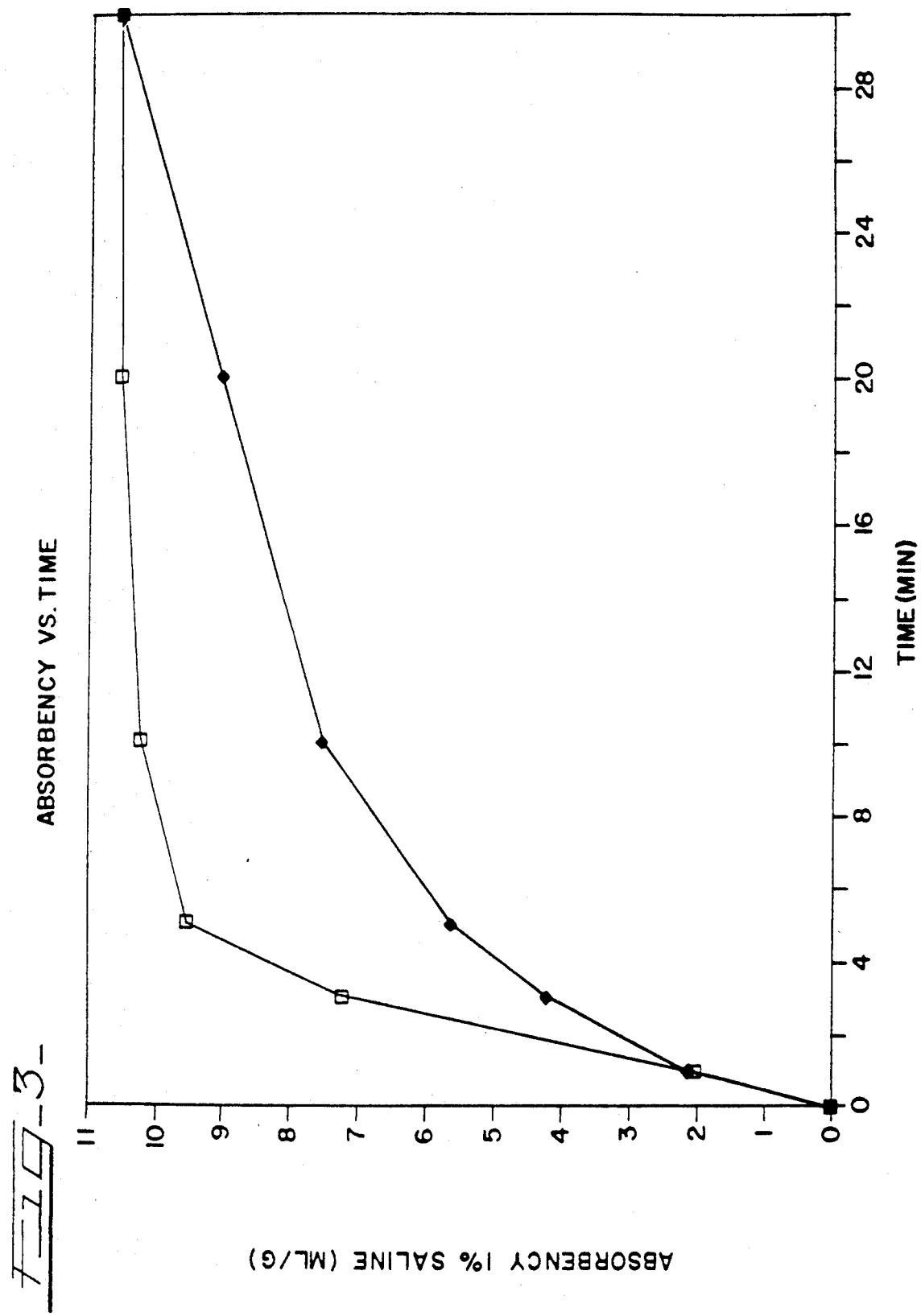

ABSORBENT ARTICLE

This application is a division, of application Ser. No. 07/772,772, filed Oct. 7, 1991, now U.S. Pat. No. 5,171,237, which is a division of application Ser. No. 07/365,967, filed Jun. 14, 1989, now U.S. Pat. No. 5,100,397.

TECHNICAL FIELD OF THE INVENTION

This invention pertains to an absorbent mixture comprising superabsorbent particles and fragments of superabsorbent polymer bound to fibrous materials, and to an absorbent article including such a mixture. This invention pertains also to a method of making such a mixture. Since the absorbent mixture is capable of absorbing liquid human excreta, such as urine, menses, and wound excreta, the absorbent mixture may be advantageously employed in making an absorbent article useful in a disposable diaper, tampon, sanitary napkin, wound dressing, or similar article.

BACKGROUND OF THE INVENTION

Detailed discussions of absorbent articles employing superabsorbent materials in disposable diapers and other products are included in Pieniak et al. U.S. Pat. Nos. 4,500,315, 4,540,454, 4,537,590, and 4,573,988, which collectively provide useful background for this invention.

As discussed in the Pieniak et al. patents noted above, absorbent articles can be advantageously made with absorbing layers and wicking layers. The absorbing layers can be advantageously made from polyester fibers, within which particles of superabsorbent material are dispersed. The wicking layers can be advantageously made from cellulosic fibers, which can include or be provided in the form of a densified, paper-like layer, such as is disclosed in Burgeni U.S. Pat. No. 3,017,304, on one side or each side. See, also, Mesek et al. U.S. Pat. No. 3,612,055 and Repke U.S. Pat. No. 3,938,522.

As also discussed in the Pieniak et al. patents noted above, the superabsorbent material can be advantageously formed from a polymerizable, cross-linkable material, e.g., a water-soluble monomer exemplified by sodium, potassium, or ammonium acrylate, which is coated, in a liquid carrier, e.g., in an aqueous solution, onto a fibrous web, and which is polymerized and cross-linked in situ, so as to form a hydrophilic polymer, which has superabsorbent properties.

Conventional coating techniques involve flooding the fibrous web with the material, in the liquid carrier, while the fibrous web is supported on a screen, so as to saturate the fibrous web, and exposing the saturated web to a partial vacuum, which removes excess amounts of the material, in the liquid carrier. It has been heretofore known to remove excess amounts of liquid by means of a padder or squeeze roll, after the fibrous web has been saturated, with similar results.

As an alternative to conventional coating techniques discussed above, it has been heretofore known to spray droplets of such a material, in a liquid carrier, by means of nozzles.

It also has been heretofore known that polymerization and cross-linking in situ can be advantageously effected by electron beam irradiation. Other techniques for polymerizing and cross-linking have been heretofore known, e.g., chemical initiation, which may require a catalyst or initiator of a known type, and heating by conventional heating means.

Although the Pieniak et al. patents noted above disclose useful products and useful methods of manufacturing such products, there has been a need, heretofore, for absorbent articles offering superior wicking and absorbent properties.

Herein, each reference to a polymerizable, cross-linkable material, in a liquid carrier, is intended to refer to any suitable monomer, oligomer, or polymer of low molecular weight, as exemplified by but not limited to a sodium, potassium, or ammonium salt of acrylic or methacrylic acid, together with a sufficient quantity of any catalyst or initiator needed to catalyze or initiate polymerizing and cross-linking of the monomer, oligomer, or polymer of low molecular weight, in a solution or suspension in a liquid carrier, as exemplified by but not limited to water. Moreover, as and where appropriate, each reference to a polymer is intended to refer to a heteropolymer or a polymer of a usual structure.

Herein, each reference to a material having absorbent properties is intended to refer to a material capable of absorbing liquid human excreta, such as urine, menses, or wound excreta. Moreover, each reference to a material having superabsorbent properties is intended to refer to a material capable of absorbing many times its own weight of such human excreta.

SUMMARY OF THE INVENTION

This invention provides an absorbent mixture having superior wicking and absorbent properties. Broadly, the absorbent mixture comprises first particles, each comprised of a polymerized, cross-linked material having absorbent properties, and second, two-phase particles, each having a fibrous phase comprised of fibers and a polymerized, cross-linked phase comprised of fragments of such material bound to fibers of the first phase. At least some of the first particles and at least some of the fragments are broken from larger particles of such material. The absorbent mixture may be advantageously employed in the manufacture of an absorbent article useful in a disposable diaper, tampon, sanitary napkin, wound dressing, or similar product requiring high absorbency.

According to this invention, the absorbent mixture is made from fibers formed into a fibrous body, e.g., a nonwoven web, and a polymerizable, cross-linkable material, in a liquid carrier. Fibers of many different types are useful, such as rayons, cellulose esters, proteins, polyamides, polyesters, polyvinyls, polyolefins, polyurethanes, glass, and mixtures thereof. Polymerizable, cross-linkable materials of many different types having absorbent or superabsorbent properties when polymerized and cross-linked, in liquid carriers, are useful, such as a sodium, potassium, or ammonium salt of acrylic or methacrylic acid, in an aqueous solution wherein water is the liquid carrier. Such a salt, when polymerized and cross-linked, results in a superabsorbent polymer.

The polymerizable, cross-linkable material, in the liquid carrier, is dispersed within the fibrous body, as dispersed inclusions. The polymerizable, cross-linkable material is polymerized and cross-linked in situ, within the fibrous body, so as to form a composite body. The composite body comprises the fibrous body and the polymerized, cross-linked material, as dispersed particles, at least some of which are bound to fibers from the fibrous web.

The absorbent mixture results from the composite body being ground, so as to cause some of the polymerized, cross-linked material to become particulate, as powder or granules, whereby the first particles are formed, while fragments of the polymerized, cross-linked material remain bound to fibers from the fibrous body, whereby the second particles are formed. The material that becomes particulate and the material that remains bound to fibers from the fibrous web account for the polymerized, cross-linked material bound to fibers from the fibrous web, in the composite body before the composite body is ground.

The composite body may be optionally provided, before it is ground, with at least one layer of fibers formed into a fibrous layer in intimate contact with the fibrous body having such inclusions. Such a layer may be optionally provided on each side of the fibrous body having such dispersed particles. If so, the fibers of the fibrous layer, or fibrous layers, may be advantageously made from comminuted wood pulp. The composite body may be intermediately processed, e.g., compressed, before the composite body is ground.

Fragments of the polymerized, cross-linked material remain bound to fibers from the fibrous body and strengthen the fibers to which such fragments are bound, whereby particulates having fibrous matrices including such strengthened fibers tend to retain their bulk when wetted with a liquid being absorbed, e.g., with urine being absorbed in a disposable diaper. Hence, the absorbent mixture exhibits superior wicking properties with less tendency for gel blocking. Gel blocking occurs if particles of a superabsorbent polymer tending to form a gel when swelling with a liquid being absorbed are too densely distributed within an absorbent article, so that the swelling particles tend to form a gel layer, which blocks additional liquid from penetrating.

The absorbent mixture exhibits superior absorbent properties, not only in terms of its efficiency as absorbent material but also in terms of its rate of absorbency, particularly as compared to absorbent structures containing similar amounts of fibers of the same types and in the same ratios and similar amounts of a superabsorbent polymer of the same type, on a weight basis. The absorbent mixture may be advantageously employed, therefore, in the manufacture of an absorbent article useful in a disposable diaper, tampon, sanitary napkin, wound dressing, or similar product benefiting from superior absorbency.

These and other objects, features, and advantages of this invention are evident from the following description of a preferred mode for carrying out this invention with reference to the accompanying drawings.

BRIEF DESCRIPTION OF THE DRAWINGS

FIG. 1 is a flow diagram representing certain steps in the manufacture of an absorbent mixture according to this invention.

FIG. 2 is a fragmentary view taken along one edge of an absorbent article including layers of an absorbent mixture manufactured as represented in FIG. 1.

FIG. 3 is a graph showing comparative properties of two samples, one being a sample of an absorbent mixture according to this invention.

DETAILED DESCRIPTION OF PREFERRED MODE

While the present invention is susceptible of embodiment in various forms, there is shown in the drawings and will hereinafter be described a presently preferred embodiment, with the understanding that the present disclosure is to be considered as an exemplification of the invention and is not intended to limit the invention to the specific embodiment illustrated.

This invention provides an absorbent mixture A comprising a novel mixture of particles of two types, which may be conveniently called first and second particles, and having superior wicking and absorbent properties.

Each of the first particles is comprised of a polymerized, cross-linked material having absorbent properties, preferably a superabsorbent polymer of a known type used in disposable diapers, tampons, sanitary napkins, or wound dressings, e.g., sodium, potassium, or ammonium polyacrylate produced by polymerizing and cross-linking a sodium, potassium, or ammonium salt of acrylic or methacrylic acid, as provided in an aqueous solution wherein the salt has been partially neutralized, and wherein the liquid carrier is water. A preferred example of such a solution is a 65% concentration (by weight) of a 55% neutralized (on a mole basis) potassium salt of acrylic acid, as neutralized with a 45% potassium hydroxide solution.

Each of the second particles has a fibrous phase comprised of fibers and a polymerized, cross-linked phase comprised of fragments of the polymerized, cross-linked material bound to fibers of the fibrous phase. At least some of the first particles and at least some of the fragments are broken from larger particles of such material. This invention allows for possibilities that some of the first particles, some of the fragments, or both are unbroken. The absorbent mixture A can be advantageously made by a method to be next described.

Initially, a fibrous web W is provided along with a polymerizable, cross-linkable material, in a liquid carrier, from any suitable source S. When polymerized and cross-linked, the polymerizable, cross-linkable material results in the polymerized, cross-linked material noted above. Thus, an aqueous solution according to the preferred example noted above may constitute the polymerizable, cross-linkable material, in the liquid carrier.

The fibrous web W is formed of fibers selected from rayons, cellulose esters, proteins, polyamides, polyesters, polyvinyls, polyolefins, polyurethanes, glass, or mixtures thereof. Preferably, the fibrous web W comprises poly(ethylene terephthalate) fibers of a type having a hollow core, as available commercially under the trademark HOLLOFIL from E. I. DuPont de Nemours and Company, Wilmington, Del., and sheath-core fibers, each having a core of poly(ethylene terephthalate) and a sheath of polyethylene, as carded into a nonwoven web having a basis weight of 1.2 oz/yd$^2$ and thermally bonded by subjecting the nonwoven web to air heated to about 275° F. and pulled through the nonwoven web while the nonwoven web is supported on a screen (not shown) in a known manner.

In a dispersing zone $Z_1$, the polymerizable, cross-linkable material, in the liquid carrier, is dispersed within the fibrous web W, as dispersed inclusions including the liquid carrier. Conventional coating techniques or alternative spraying techniques are useful to disperse the polymerizable, cross-linkable material, in the liquid carrier, within the fibrous web W.

Conventional coating techniques involve flooding the fibrous web W with the polymerizable, cross-linkable material, in the liquid carrier, while the fibrous web W is supported on a screen (not shown), so as to saturate the fibrous web W, and exposing the saturated web W to a partial vacuum, which removes excess amounts of the polymerizable, cross-linkable material, in the liquid carrier. Excess amounts of liquid may be alternatively removed by means of a padder or squeeze roll (not shown), after the fibrous web W has been saturated, with similar results. Whichever approach is used to remove excess amounts of liquid, the fibrous web W tends to retain the polymerizable, cross-linkable material, in the liquid carrier, as dispersed inclusions including the liquid carrier, bridging adjacent fibers of the fibrous web W, and being held by fiber-to-fiber capillaries.

If alternative spraying techniques are used to disperse the polymerizable, cross-linkable material, in the liquid carrier, within the fibrous web W, droplets of the polymerizable, cross-linkable material, in the liquid carrier, may be thus sprayed, as by means of nozzles, onto opposite sides of the fibrous web W as the fibrous web W is moved through the dispersing zone $Z_1$. The fibrous web W tends to retain such droplets as dispersed inclusions including the liquid carrier, bridging adjacent fibers of the fibrous web W, and being held by fiber-to-fiber capillaries.

After the polymerizable, cross-linkable material M, in the liquid carrier, has been dispersed within the fibrous web W, as dispersed inclusions including the liquid carrier, the fibrous web W retaining such inclusions is moved to a polymerizing and cross-linking zone $Z_2$, in which the material M is polymerized and cross-linked in situ, within the fibrous web W, so as to form a composite web W comprising the fibrous web W and the polymerized, cross-linked material, as dispersed particles, some most, or all of which are bound to fibers from the fibrous web W. This invention allows for a possibility that some of the dispersed particles may not be so bound but may be loosely retained within the composite web W'. However, dispersed particles bound to fibers from the fibrous web W constitute the larger particles noted above, from which at least some of the first particles and at least some of the fragments are broken.

Any suitable means (not shown) for electron beam irradiation is preferred as a means for polymerizing and cross-linking the material M; an example is an Energy Sciences ™ (Model CB300) accelerator, as available from Energy Sciences, Inc. If electron beam irradiation is used, the fibrous web W retaining the material M, in the liquid carrier, in dispersed inclusions may be initially exposed to 2 MRAD of such radiation on each side of the fibrous web W, and finally exposed to a curing dose of 8 MRAD on each side of the fibrous web W. Any other suitable technique for electron beam irradiation may be instead used.

Any other suitable technique for polymerizing and cross-linking the material M in situ may be instead used, e.g., chemical initiation, which may require a catalyst or initiator of a known type.

The composite web W' contains dispersed particles of the polymerized, cross-linked material M from which substantially all of the liquid carrier has evolved. If the polymerizable, cross-linkable material, in the liquid carrier, is an aqueous solution according to the preferred example given above, such particles are comprised of sodium polyacrylate, from which substantially all of the liquid carrier, i.e., water, has evolved.

The composite web W' may be intermediately processed in known ways. The composite web W' may be provided, on each side, with a fibrous layer, e.g., a nonwoven layer of fibers from comminuted wood pulp or other cellulosic fibers, in intimate contact with the fibrous web having such inclusions of the polymerized, cross-linked material. The facing layers may be also provided with a densified, paper-like layer (not shown) in a manner disclosed in the Burgeni, Mesek et al., and Repke patents noted above. Moreover, the composite web W' may be then compressed, so as to increase its density.

It is to be here understood that the composite web W' is made and may be intermediately processed by methods similar to methods disclosed in the Pieniak et al. and other patents noted above. Thus, the composite web W' is useful apart from this invention, as an absorbent article of a type disclosed in the Pieniak et al. patents noted above.

According to this invention, however, the composite web W', after any such intermediate processing step has been completed, is moved to a grinding zone $Z_3$, in which the composite web W' is ground, as by means of a grinding mill (not shown), so as to form the first and second particles. At least some of the dispersed particles retained by the composite web W' are broken, as the composite web W' is ground, so as to produce the first particles from the broken particles that had been bound to fibers from the fibrous web W', from any broken particles that had been retained by the composite web W' but were not bound to fibers from the fibrous web W, and from any particles that had been retained by the composite web W' but were not bound to fibers from the fibrous web W and were not broken, and so as to form the fragments bound to fibers from the fibrous web W from the broken particles that had been bound to fibers from the fibrous web W and from any particles that had been bound to fibers from the fibrous web W but were not broken.

Preferably, the absorbent mixture A comprises, on a weight basis, about 5 to 40% of fibers from the fibrous web W, more preferably about 10% of fibers from the fibrous web W, with the balance consisting essentially of a superabsorbent polymer. More preferably, the absorbent mixture A comprises, on a weight basis, about 10% of fibers from the fibrous web W, also about 30 to 80% of the superabsorbent polymer, most preferably about 50% of the superabsorbent polymer, as particles, i.e., powder or granules, and about 10 to 60% of the superabsorbent polymer, most preferably about 40% of the superabsorbent polymer, as fragments bound to at least some fibers from the fibrous web W. A most preferred composition for the absorbent mixture A, on a weight basis, is, therefore, about 10% of fibers from the fibrous web W, about 50% of the superabsorbent polymer, as particles, i.e., powder or granules, an about 40% of the superabsorbent polymer, as fragments bound to at least some fibers from the fibrous web W.

When the composite web W is ground, fragments of the polymerized, cross-linked material M remain bound to fibers from the fibrous web W and strengthen the fibers to which such fragments are bound. Particles produced by grinding of the composite web W' with fibrous phases including such strengthened fibers tend to retain their bulk when wetted with a liquid being absorbed by the polymerized, cross-linked material M, e.g., with urine being absorbed in a disposable diaper. Since the liquid can channel through the absorbent mixture by capillary action to be then absorbed by the polymerized, cross-linked material M, the absorbent mixture A exhibits superior wicking properties with less tendency for gel blocking, which is explained above.

Furthermore, the absorbent mixture A exhibits superior absorbent properties, not only in terms of its efficiency as absorbent material but also in terms of its rate of absorbency, as compared to a composite web comprising fibers of the same types and in the same ratios and a superabsorbent polymer of the same type, for equivalent basis weights of the superabsorbent polymer.

As shown fragmentarily in FIG. 2, an absorbent article 10 useful in a disposable diaper having conventional backing and facing layers (not shown) comprises a relatively thick, nonwoven fibrous layer 12 of fibers from comminuted wood pulp, a relatively thick layer 14 of a ground, absorbent mixture according to this invention, in intimate contact with the fibrous layer 12, an intermediate layer 16 of a composite web similar to the composite web described above, in intimate contact with the layer 14 of the absorbent mixture, and a relatively thin, nonwoven, fibrous layer 18 of fibers from comminuted wood pulp. In FIG. 2, the intermediate layer 16 of a composite web and the layer 14 of the absorbent mixture are demarcated approximately by dashed lines.

As one example, the absorbent article 10 may be advantageously made by casting the relatively thin, nonwoven, fibrous layer 18 with a basis weight of 2.6 oz/yd$^2$ onto one expansive surface of the composite web to constitute the intermediate layer 16, such web having a basis weight of 1.2 oz/yd$^2$ and an add-on ratio of 3:1, inverting the resulting two-layer structure, distributing the relatively thick layer 14 of the ground, absorbent mixture with a basis weight of 9.7 oz/yd$^2$ after grinding onto the opposite surface of the fibrous layer 18, and casting the relatively thick, nonwoven, fibrous layer 12 with a basis weight of 5.2 oz/yd$^2$ onto the exposed, expansive surface of the layer 14 of the ground, absorbent mixture. Desirably, the relatively thin, nonwoven, fibrous layer 18 tends to retain any small particles that tend to sift from the layer 14 of the ground, absorbent mixture through the composite web constituting the intermediate layer 16. In the example, the ground, absorbent mixture results from grinding a composite web with a basis weight of 1.2 oz/yd$^2$ and an add-on ratio of 10:1, before grinding. The composite web to constitute the intermediate layer 16 may be pre-compressed, i.e., compressed before the relatively thin, nonwoven, fibrous layer 18 is cast. All basis weights noted above are approximate.

Although the absorbent article 10 has been described as having layers, it is to be here understood that the materials of such layers tend to commingle. As an example, some of the ground, absorbent material of the layer 14 tends to migrate into the fibrous structure of the composite web constituting the layer 16. All references herein to layers are intended to be so understood.

In the absorbent article 10, the fibrous layers 12, 18, are regarded as wicking layers even if either such layer tends to remain dry, whereas the layers between the fibrous layers 12, 18 are regarded as absorbing layers. Such designations of layers as wicking layers and absorbing layers are not intended as limiting, however, since the fibrous layers 12, 18, ordinarily exhibit some absorbency and the fibers of the layers between the fibrous layers 12, 18, have good wicking capabilities. The absorbent article 10 exhibits a gradient of different absorbencies at its respective layers. In a disposable diaper, the thicker, fibrous layer 12 is to be preferably disposed so as to face the backing layer, which is liquid-impervious, not the facing layer, which is liquid-pervious.

For comparable amounts of a superabsorbent polymer, the absorbent article 10 provides numerous advantages over absorbent articles known heretofore. Thus, the absorbent article 10 exhibits a faster rate of absorbency, which may be plausibly explained by different rates of absorbency within the absorbent article 10, particularly in the ground, absorbent material constituting the layer 14 and the composite web constituting the layer 16. Also, the absorbent article 10 exhibits less leakage, which may be similarly explained. A greater portion of the superabsorbent polymer tends to contact the fibrous material of the absorbent article 10, particularly the relatively thick, nonwoven, fibrous layer 12, which acts as a wicking layer. The relatively thin, nonwoven, fibrous layer 18 tends to remain drier.

Moreover, the superabsorbent polymer tends to swell to a higher capacity, which tends to be less restricted by the fibrous materials, particularly in the ground, absorbent material constituting the layer 14. The higher capacity of the superabsorbent polymer provides the absorbent article 10 with a higher capacity and with less tendency to leak. Furthermore, since much of the superabsorbent polymer is present in the ground, absorbent material constituting the layer 14, rather than in the composite web constituting the layer 16, there is less need for softening, or tenderizing, to condition the absorbent article 10 for its use in a disposable diaper.

As developed from comparative tests, FIG. 3 is a graph plotting, for each of two samples, absorbency of a test liquid versus time. The test liquid, for each of these samples, was an aqueous solution of 1% by weight of sodium chloride. Absorbency was measured as demand absorbency, under a sample pressure of 0.5 psig and a 1.5 cm negative head of the test liquid. The absorbed volume was measured after one minute and after three, five, nine, twenty, and thirty minutes, as indicated on the graph. Demand absorbency was measured as described in McConnell U.S. Pat. No. 4,357,827.

In FIG. 3, the upper plot represents a first sample, of an absorbent mixture according to this invention, as made from a fibrous web comprising fibers of a type having a hollow core, as available commercially under the trademark HOLLOFIL from E. I. DuPont de Nemours and Company, Wilmington, Del., as carded into a nonwoven web having a basis weight of 1.2 oz/yd$^2$ and thermally bonded by subjecting the nonwoven web to air heated to about 275° F. and pulled through the nonwoven web while the nonwoven web was supported on a screen, and an aqueous solution of 65% concentration (by weight) of a 55% neutralized (on a mole basis) potassium salt of acrylic acid, as neutralized with a 45% potassium hydroxide solution.

The fibrous web was flooded with the aqueous solution, while the fibrous web was supported on a screen, so as to saturate the fibrous web. The saturated web was exposed to a partial vacuum, which removed excess amounts of the aqueous solution. The material in the aqueous solution was polymerized and cross-linked in situ, within the fibrous web, so as to form a composite web. The material in the aqueous solution was polymerized and cross-linked by electron beam irradiation with an initial exposure of 2 MRAD on each side of the fibrous web and with a curing dose of 8 MRAD on each side of the fibrous web.

The composite web was ground into particulates, so as to form the first sample, which on a weight basis consisted essentially of about 10% of the fibers from the fibrous web, about 50% of the polymerized, cross-linked material, as particles, and about 40% of the polymerized, cross-linked material, as fragments bound to at least some fibers from the fiberous web. The polymerized, cross-linked material present in the first sample is a typical example of a superabsorbent polymer, as used in disposable diapers and other products requiring high absorbency.

In FIG. 3, the lower plot represents a second sample, which consisted essentially of a composite web containing polymerized, cross-linked material like the composite web containing polymerized, cross-linked material in the first sample, the polymerized, cross-linked material in the second sample having a basis weight about equal to the basis weight of the polymerized, cross-linked material present in the first sample. The second sample was not ground into particulates.

It has been concluded, from the results plotted in FIG. 3, that an absorbent mixture according to this invention has superior absorbent properties, not only in terms of its efficiency as absorbent material but also in terms of its rate of absorbency, as compared to other structures containing a superabsorbent material of the same type, for equivalent basis weights of the superabsorbent material.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover by the appended claims all such modifications as fall within the scope of the claims.

What is claimed is:

1. An absorbent article comprising a first absorbent layer and a second absorbent layer, said first absorbent layer comprising (a) first particles, each comprised of a polymerized, cross-linked material, and (b) second, two-phase particles, each having a fibrous phase comprised of particles of fibers and a polymerized, cross-linked phase comprised of fragments of said cross-linked material bound to particles of fibers of the fibrous phase, said first particles being loosely dispersed within said second particles, said second absorbent layer including a fibrous body and inclusions of said cross-linked material, as polymerized and cross-linked in situ within the fibrous body of said second absorbent layer, the first and second particles being distributed in intimate contact with an expansive surface of the second absorbent layer.

2. An absorbent article comprising a first absorbent layer and a second absorbent layer, said first absorbent layer being formed from a fibrous body including polymerized, cross-linked material having absorbent properties, at least some of which material is bound to fibers of said fibrous body, said first absorbent layer comprising (a) first particles, each comprised of said polymerized, cross-linked material, and (b) second, two-phase particles, each having a fibrous phase comprised of particles of said fibers, and a polymerized, cross-linked phase comprised of fragments of said cross-linked material bound to the particles of fibers of the fibrous phase, wherein at least some of the first particles and at least some of the fragments are broken from larger particles of said cross-linked material after said cross-linked material is bound to the fibers from which said particles of fibers of said fibrous phase are formed, said first particles being loosely distributed within said second particles, wherein said fibers from which said particles of fibers are formed are first formed in said fibrous body and said cross-linked material is provided in a liquid carrier before polymerizing and cross-linking, said material being dispersed within the fibrous body as dispersed inclusions, including the liquid carrier before polymerizing and cross-linking, and being polymerized and cross-linked in situ, within the fibrous body, so as to form a composite body comprising the fibrous body and the polymerized, cross-linked material, as dispersed particles, at least some of which are bound to the fibers from the fibrous body, the composite body being ground so as to cause some of the polymerized, cross-linked material from the dispersed particles to become particulate, whereby said first particles of cross-linked material are formed, while fragments of the polymerized, cross-linked material from the dispersed particles remain bound to the particles of fibers from the fibrous body, whereby the second two-phase particles are formed, said second absorbent layer including a fibrous body and inclusions of said cross-linked material, as polymerized and cross-linked in situ within the fibrous body of said second absorbent layer, the first and second particles of the first absorbent layer being distributed in intimate contact with an expansive surface of the second absorbent layer.

3. The absorbent article of claim 2 wherein said material, as polymerized and cross-linked, is a superabsorbent polymer.

4. The absorbent article of claim 2 further comprising a wicking layer of fibrous material in intimate contact with an expansive surface of one of the absorbent layers.

5. The absorbent article of claim 4 wherein said material, as polymerized and cross-linked, is a superabsorbent polymer.

6. The absorbent article of claim 2 further comprising a first wicking layer of fibrous material in intimate contact with an expansive surface of the first absorbent layer and a second wicking layer in intimate contact with an expansive surface of the second absorbent layer.

7. The absorbent article of claim 6 wherein said material, as polymerized and cross-linked, is a superabsorbent polymer.

8. A two-phase, absorbent particle having a fibrous phase comprised of fibers, and a polymerized, cross-linked material bound to fibers from the fibrous phase, dispersing a polymerizable cross-linkable material, in a liquid carrier, within a fibrous body, polymerizing and cross-linking the polymerizable, cross-linkable material in situ, within the fibrous body, so as to form a composite body, said composite body comprising the fibrous body and dispersed particles of the polymerized, cross-linked material bound to fibers from the fibrous body; and subdividing the fibrous body to form said particle.

9. A two-phase, absorbent particle according to claim 8 wherein the composite body is subdivided by grinding to form said particle.

10. A two-phase absorbent particle according to claim 9, in an absorbent mixture with additional particles, which include similar two-phase absorbent particles and particles of the polymerized, cross-linked material, with the particles of the polymerized, cross-linked material being dispersed freely in the absorbent mixture.

* * * * *

UNITED STATES PATENT AND TRADEMARK OFFICE
CERTIFICATE OF CORRECTION

PATENT NO. : 5,246,429
DATED : September 21, 1993
INVENTOR(S) : John F. Poccia, et al.

It is certified that error appears in the above-indentified patent and that said Letters Patent is hereby corrected as shown below:

```
In column 10, line 48, after "phase," insert --said
            particle being formed by--
```

Signed and Sealed this

Twelfth Day of April, 1994

Attest:

BRUCE LEHMAN

*Attesting Officer*    *Commissioner of Patents and Trademarks*